(12) United States Patent  
Kudis et al.

(10) Patent No.: US 6,903,221 B2
(45) Date of Patent: Jun. 7, 2005

(54) METHOD FOR PRODUCING β-KETOENOL ESTERS

(75) Inventors: Steffen Kudis, Mannheim (DE); Ulf Misslitz, Neustadt (DE); Ernst Baumann, Dudenhofen (DE); Wolfgang von Deyn, Neustadt (DE); Klaus Langemann, Schauenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 161 days.

(21) Appl. No.: 10/362,056

(22) PCT Filed: Aug. 21, 2001

(86) PCT No.: PCT/EP01/09672

§ 371 (c)(1),
(2), (4) Date: Feb. 20, 2003

(87) PCT Pub. No.: WO02/16305

PCT Pub. Date: Feb. 28, 2002

(65) Prior Publication Data

US 2003/0191318 A1 Oct. 9, 2003

(30) Foreign Application Priority Data

Aug. 22, 2000 (DE) .......................................... 100 41 044

(51) Int. Cl.⁷ .......................... C07D 261/04; C07C 67/36
(52) U.S. Cl. ..................... 548/313.1; 560/106; 560/113
(58) Field of Search ....................... 548/313.1; 560/106, 560/113

(56) References Cited

U.S. PATENT DOCUMENTS

| 5,744,425 A | 4/1998 | Plath et al. |
| 6,004,903 A | 12/1999 | Von Deyn et al. |

OTHER PUBLICATIONS

Tetrahedron Letters, vol. 37, No. 7, 100–1010, Montes et al.
Tetrahedron Letters, vol. 31, No. 20, 2841–2844, 1990, Shimoyama et al.

*Primary Examiner*—Kamal Saeed
(74) *Attorney, Agent, or Firm*—Novak Druce & Quigg, LLP

(57) ABSTRACT

The invention relates to a method for producing β-ketoenol esters of the general formula (Ia) or (Ib), wherein Ar, $R^a$ and $R^b$ are defined as in claim 1. The inventive method is characterized by reacting an arylhalogenide of the general formula (II) with a 1,3-diketone of the general formula (III) or the tautomers thereof in a carbon monoxide atmosphere in the presence of an alkali and a catalyst that contains at least one transition metal of group VIII of the periodic system

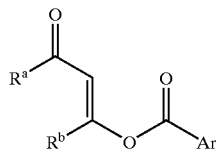

(Ia)

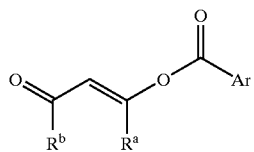

(Ib)

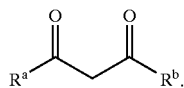

(III)

12 Claims, No Drawings

METHOD FOR PRODUCING β-KETOENOL ESTERS

The present invention relates to a process for preparing β-ketoenol esters of the formulae Ia and Ib

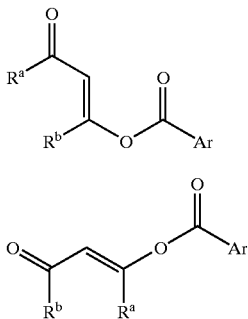

in which
$R^a$, $R^b$ independently of one another are $C_1$–$C_6$-alkyl or $C_3$–$C_8$-cycloalkyl, or
$R^a$ and $R^b$ together are $C_2$–$C_4$-alkanediyl or $C_5$–$C_7$-cycloalkanediyl, where the three groups mentioned above may be substituted or unsubstituted and may have a fused 3-, 4-, 5- or 6-membered saturated carbocycle, a spiro-linked 3-, 4-, 5- or 6- or 7-membered saturated carbocycle, a spiro-linked 3-, 4-, 5-, 6- or 7-membered saturated heterocycle having 1 or 2 chalkogen atoms, selected from the group consisting of oxygen and sulfur and/or a carbonyl or thiocarbonyl group;
Ar is phenyl or pyridyl, which may in each case have 1, 2, 3 or 4 substituents, it also being possible for two substituents attached to adjacent carbon atoms to form, together with these atoms, a 5- or 6-membered saturated or unsaturated carbocycle or a 5- or 6-membered saturated or unsaturated heterocycle which has 1, 2 or 3 hetero atoms selected from the group consisting of O, N and S and which for its part may be substituted or unsubstituted.

β-Ketoenol esters of aromatic carboxylic acids which correspond to the formulae Ia and Ib defined above are interesting intermediates for preparing herbicidally active 2-aroyl-1,3-diketones of the formula X:

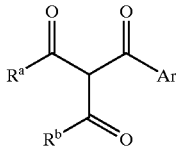

in which $R^a$, $R^b$ and Ar are as defined above.

Herbicidallly active 2-aroyl-1,3-diketones are disclosed, for example, in EP-A 90262, EP-A 135191, EP-A 162166, EP-A 186118, EP-A 186119, EP-A 283261, EP-A 319075, WO 90/05712, WO 94/04524, WO 94/08988, JP 3052862, JP 3120202, WO 96/04182, WO 97/09324, WO 99/03845 and Weed Science, 45 (1997), 601–609 and the literature cited therein.

The 2-aroyl-1,3-diketones are generally prepared starting with an aromatic carboxylic acid of the formula Ar—COOH or its acyl chloride Ar—CO—Cl, which is reacted with a 1,3-diketone of the formula III $$R^a\text{—C(O)—CH}_2\text{—C(O)—}R^b \quad (III)$$

or its tautomer III' or III"

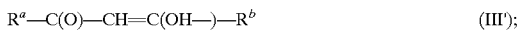

in which $R^a$ and $R^b$ are as defined above in the presence of a dehydrating agent, for example an anhydride or a carbodiimide, to give β-ketoenol esters of the formula I defined above.

The β-ketoenol esters I are then rearranged with a base, preferably in the presence of a catalytically effective amount of a cyanide-group-containing compound, to give the herbicidally active 2-aroyl-1,3-diketones of the formula X defined above. In place of the carboxylic acid Ar—COOH, it is also possible to employ an activated aryl carboxylic acid derivative, for example a carbonyl halide Ar—COL, in which L is a halogen atom, such as chlorine, for preparing β-ketoenol esters I. The reaction of the acid halide with III to give I is preferably carried out in the presence of a base (cf. the abovementioned prior art, in particular EP 283261 and WO 96/05182, and the literature cited therein).

This process has the disadvantage that the aromatic carboxylic acids Ar—COOH have to be prepared in a complicated manner, for example from the more easily accessible aryl halides, for example by successive conversion into an organometallic compound and subsequent reaction with $CO_2$, or by side-chain oxidation of ethyl-substituted aromatics.

In particular in the case of aromatic compounds having fused heterocycles, the preparation of the carboxylic acids Ar—COOH is not without problems. The subsequent reaction of the arylcarboxylic acids Ar—COOH or their activated derivatives Ar—COL into the β-ketoenol esters I can likewise not always be realized with satisfactory yields.

It is an object of the present invention to provide a more economical process for preparing β-ketoenol esters of the formula I.

We have found that this object is achieved by reacting aryl halides of the formula II $$Ar\text{-Hal} \quad (II)$$

in which Ar is as defined above and Hal is a halogen atom selected from the group consisting of chlorine, bromine and iodine with a 1,3-diketone of the formula III or its tautomer III' or III" in a carbon monoxide atmosphere in the presence of a base and a catalyst which comprises at least one transition metal of group VIII of the Periodic Table of the Elements, which, surprisingly, gives the β-ketoenol esters of the formula I defined above in good yields.

Accordingly, the present invention relates to a process for preparing β-ketoenol esters of the formula Ia or Ib defined at the outset, which process comprises reacting an aryl halide of the formula II defined above with a 1,3-diketone of the formula III or its tautomer III' or III" in a carbon monoxide atmosphere in the presence of a base and a catalyst which comprises at least one transition metal of group VIII of the Periodic Table of the Elements.

The present invention furthermore relates to a process in which initially an aryl halide of the formula II is reacted with a 1,3-diketone of the formula III or its tautomer III' or III" in a carbon monoxide atmosphere in the presence of the base and a catalyst which comprises at least one transition metal of group VIII of the Periodic Table of the Elements to give a β-ketoenol ester of the formula Ia or Ib defined at the outset, and then rearranging this β-ketoenol ester by treatment with a base and a catalytically effective amount of at least one cyanide compound into 2-aryl-substituted 1,3-diketones of the formula X or their tautomers Xa, Xb or Xc.

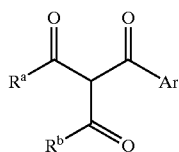
(X)

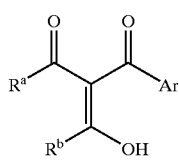
(Xa)

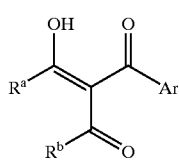
(Xb)

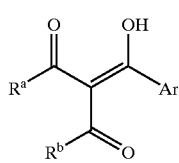
(Xc)

The organic molecular moieties mentioned for the substituents $R^a$, $R^b$ and Ar or below as radicals on phenyl and heterocyclyl radicals are collective terms for individual enumerations of the individual group members. All hydrocarbon chains, i.e. all alkyl, haloalkyl, alkoxy, haloalkoxy, alkylthio, haloalkylthio, alkylsulfinyl, alkylsulfonyl, N-alkylamino, N,N-dialkylamino, alkylcarbonyl, alkoxycarbonyl, alkylcarbonyloxy, alkylaminocarbonyl, dialkylaminocarbonyl, alkoxyalkyl, alkoxyiminoalkyl, phenylalkyl, heterocyclylalkyl, alkenylcarbonyl, alkenyloxycarbonyl, alkenyl, alkynyl, haloalkenyl, haloalkynyl, alkenyloxy, alkynyloxy, alkanediyl, alkenediyl, alkanediendiyl or alkyndiyl moieties can be straight-chain or branched. The term $C_n$–$C_m$ indicates the number of possible carbon atoms. Unless indicated otherwise, halogenated substituents preferably carry one to five identical or different halogen atoms. The term halogen denotes in each case fluorine, chlorine, bromine or iodine.

Examples of other meanings are:

$C_1$–$C_4$-alkyl and the alkyl moieties of (di)-$C_1$–$C_4$-alkylamino, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkylcarbonyl, $C_1$–$C_4$-alkoxycarbonyl, $C_1$–$C_4$-alkyloxycarbonyl, $C_1$–$C_4$-alkylaminocarbonyl, $C_1$–$C_4$-alkylcarbonylamino: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of (di)-$C_1$–$C_6$-alkylamino, $C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylcarbonyl, $C_1$–$C_6$-alkoxycarbonyl, $C_1$–$C_6$-alkyloxycarbonyl, $C_1$–$C_6$-alkylaminocarbonyl, $C_1$–$C_6$-alkylcarbonylamino: $C_1$–$C_4$-alkyl, as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl and the haloalkyl moieties of (di)-$C_1$–$C_4$-haloalkylamino, $C_1$–$C_4$-haloalkoxy, $C_1$–$C_4$-haloalkylthio, $C_1$–$C_4$-haloalkylsulfinyl, $C_1$–$C_4$-haloalkylsulfonyl, $C_1$–$C_4$-haloalkylcarbonyl, $C_1$–$C_4$-haloalkoxycarbonyl, $C_1$–$C_4$-haloalkyloxycarbonyl, $C_1$–$C_4$-haloalkylaminocarbonyl, $C_1$–$C_4$-haloalkylcarbonylamino: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of (di)-$C_1$–$C_6$-haloalkylamino, $C_1$–$C_6$-haloalkoxy, $C_1$–$C_6$-haloalkylthio, $C_1$–$C_6$-haloalkylsulfinyl, $C_1$–$C_6$-haloalkylsulfonyl, $C_1$–$C_6$-haloalkylcarbonyl, $C_1$–$C_6$-haloalkoxycarbonyl, $C_1$–$C_6$-haloalkyloxycarbonyl, $C_1$–$C_6$-haloalkylaminocarbonyl, $C_1$–$C_6$-haloalkylcarbonylamino: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodinehexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_6$-haloalkoxy: a $C_1$–$C_6$-alkoxy radical as mentioned above which is partially or fully substituted by fluorine, chlorine, bromine and/or iodine;

$C_1$–$C_6$-alkylcarbonyl, and the alkylcarbonyl radicals of $C_1$–$C_6$-alkylcarbonyl-$C_1$–$C_6$-alkyl, $C_1$–$C_6$-alkylcarbonyloxy, $C_1$–$C_6$-alkylcarbonylamino: an alkyl radical which is attached via a carbonyl group, for example methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;

$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$–$C_6$-alkoxycarbonyl: methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

$C_1$–$C_6$-hydroxyalkyl: $C_1$–$C_6$-alkyl which is substituted by one to three OH— groups, for example hydroxymethyl, 1-hydroxyethyl, 2-hydroxyethyl, 1,2-bishydroxyethyl, 1-hydroxypropyl, 2-hydroxypropyl, 3-hydroxypropyl, 4-hydroxybutyl, 2,2-dimethyl-3-hydroxypropyl;

$C_1$–$C_6$-hydroxyalkoxy: $C_1$–$C_6$-alkoxy which is substituted by one to three OH— groups, for example hydroxymethoxy, 1-hydroxyethoxy, 2-hydroxyethoxy, 1,2-bishydroxyethoxy, 1-hydroxypropoxy, 2-hydroxypropoxy, 3-hydroxypropoxy, 4-hydroxybutoxy, 2,2-dimethyl-3-hydroxypropoxy;

phenyl-$C_1$–$C_6$-alkyl: $C_1$–$C_6$-alkyl which is substituted by a phenyl radical, for example benzyl, 1-phenylethyl and 2-phenylethyl, where the phenyl radical may, in the manner mentioned above, be partially or fully halogenated and/or may carry one to three of the substituents mentioned above for phenyl;

correspondingly, heterocyclyl $C_1$–$C_6$-alkyl is a $C_1$–$C_6$-alkyl which is substituted by a heterocyclyl radical;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy) methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

di-($C_1$–$C_6$-alkoxy)methyl: methyl which is substituted by two $C_1$–$C_6$-alkoxy groups;

di-($C_1$–$C_6$-alkylthio)methyl: methyl which is substituted by two $C_1$–$C_6$-alkylthio groups;

($C_1$–$C_6$-alkoxy)($C_1$–$C_6$-alkylthio)methyl: methyl which is substituted by one $C_1$–$C_6$-alkoxy group and by one $C_1$–$C_6$-alkylthio group;

$C_1$–$C_6$-(halo)alkylsulfonyl-$C_1$–$C_6$-alkyl, $C_1$–$C_6$-(halo)alkylthio-$C_1$–$C_6$-alkyl, $C_1$–$C_6$-alkylamino-$C_1$–$C_6$-alkyl, di-$C_1$–$C_6$-alkylamino-$C_1$–$C_6$-alkyl: $C_1$–$C_6$-alkyl which is substituted by $C_1$–$C_6$-(halo)alkylsulfonyl, $C_1$–$C_6$-(halo)alkylthio, $C_1$–$C_6$-alkylamino and di-$C_1$–$C_6$-alkylamino respectively;

$C_1$–$C_6$-alkoxy-$C_1$–$C_6$-alkoxy: $C_1$–$C_6$-alkoxy, which is substituted by $C_1$–$C_6$-alkoxy as mentioned above, i.e., for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_1$–$C_6$-alkylcarbonyl-$C_1$–$C_6$-alkyl: $C_1$–$C_6$-alkyl which is substituted by a $C_1$–$C_6$-alkylcarbonyl group, where both of the $C_1$–$C_6$-alkyl groups may carry one or more substituents selected from the group consisting of $C_1$–$C_4$-alkoxy and hydroxyl: for example acetylmethyl (=2-oxopropyl), 2-(acetyl)ethyl (=3-oxo-n-butyl), 3-oxo-n-pentyl, 1,1-dimethyl-2-oxopropyl, 3-hydroxy-2-oxopropyl or 3-hydroxy-2-oxobutyl;

$C_3$–$C_6$-alkenyl, and the alkenyl moieties of $C_3$–$C_6$alkenylcarbonyl, $C_3$–$C_6$-alkenyloxy, $C_3$–$C_6$-alkenyloxycarbonyl, $C_3$–$C_6$-alkenylaminocarbonyl, N—($C_3$–$C_6$-alkenyl)-N—($C_1$–$C_6$-alkyl)aminocarbonyl, N—($C_3$–$C_6$-alkenyl)-N—($C_1$–$C_6$-alkoxy)aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl, as mentioned above, and also ethenyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N—($C_3$–$C_6$-alkynyl)-N—($C_1$–$C_6$-alkyl)aminocarbonyl, N—($C_3$–$C_6$-alkynyl)-N—($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_2$–$C_4$-alkanediyl for $R^a$ and $R^b$: ethane-1,2-diyl, propane-1,2-diyl, propane-1,3-diyl, butane-1,2-diyl, butane-1,3-diyl, butane-1,4-diyl, in particular propane-1,3-diyl;

$C_1$–$C_6$-alkanediyl: methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-1,4-diyl, 2-methylpropane-1,3-diyl, 2-methylpropane-1,2-diyl, 2-methylpropane-1,1-diyl, 1-methylpropane-1,2-diyl, 1-methylpropane-2,2-diyl, 1-methylpropane-1,1-diyl, pentane-1,1-diyl, pentane-1,2-diyl, pentane-1,3-diyl, pentane-1,5-diyl, pentane-2,3-diyl, pentane-2,2-diyl, 1-methylbutane-1,1-diyl, 1-methylbutane-1,2-diyl, 1-methylbutane-1,3-diyl, 1-methylbutane-1,4-diyl, 2-methylbutane-1,1-diyl, 2-methylbutane-1,2-diyl, 2-methylbutane-1,3-diyl, 2-methylbutane-1,4-diyl, 2,2-dimethylpropane-1,1-diyl, 2,2-dimethylpropane-1,3-diyl, 1,1-dimethylpropane-1,3-diyl, 1,1-dimethylpropane-1,2-diyl, 2,3-dimethylpropane-1,3-diyl, 2,3-dimethylpropane-1,2-diyl, 1,3-dimethylpropane-1,3-diyl, hexane-1,1-diyl, hexane-1,2-diyl, hexane-1,3-diyl, hexane-1,4-diyl, hexane-1,5-diyl, hexane-1,6-diyl, hexane-2,5-diyl, 2-methylpentane-1,1-diyl, 1-methylpentane-1,2-diyl, 1-methylpentane-1,3-diyl, 1-methylpentane-1,4-diyl, 1-methylpentane-1,5-diyl, 2-methylpentane-1,1-diyl, 2-methylpentane-1,2-diyl, 2-methylpentane-1,3-diyl, 2-methylpentane-1,4-diyl, 2-methylpentane-1,5-diyl, 3-methylpentane-1,1-diyl, 3-methylpentane-1,2-diyl, 3-methylpentane-1,3-diyl, 3-methylpentane-1,4-diyl, 3-methylpentane-1,5-diyl, 1,1-dimethylbutane-1,2-diyl, 1,1-dimethylbutane-1,3-diyl, 1,1-dimethylbutane-1,4-diyl, 1,2-dimethylbutane-1,1-diyl, 1,2-dimethylbutane-1,2-diyl, 1,2-dimethylbutane-1,3-diyl, 1,2-dimethylbutane-1,4-diyl, 1,3-dimethylbutane-1,1-diyl, 1,3-dimethylbutane-1,2-diyl, 1,3-dimethylbutane-1,3-diyl, 1,3-dimethylbutane-1,4-diyl, 1-ethylbutane-1,1-diyl, 1-ethylbutane-1,2-diyl, 1-ethylbutane-1,3-diyl, 1-ethylbutane-1,4-diyl, 2-ethylbutane-1,1-diyl, 2-ethylbutane-1,2-diyl, 2-ethylbutane-1,3-diyl, 2-ethylbutane-1,4-diyl, 2-ethylbutane-2,3-diyl, 2,2-dimethylbutane-1,1-diyl, 2,2-dimethylbutane-1,3-diyl, 2,2-dimethylbutane-1,4-diyl, 1-isopropylpropane-1,1-diyl, 1-isopropylpropane-1,2-diyl, 1-isopropylpropane-1,3-diyl, 2-isopropylpropane-1,1-diyl, 2-isopropylpropane-1,2-diyl, 2-isopropylpropane-1,3-diyl, 1,2,3-trimethylpropane-1,1-diyl, 1,2,3-trimethylpropane-1,2-diyl or 1,2,3-trimethylpropane-1,3-diyl;

$C_3$–$C_8$-cycloalkyl, and the cycloalkyl moieties of $C_3$–$C_8$-cycloalkoxy, $C_3$–$C_8$-cycloalkylamino and $C_3$–$C_8$-cycloalkylcarbonyl: for example cyclopropyl, cyclobutyl, cyclopentyl, cyclohexyl, cycloheptyl, cyclooctyl, norbornyl, [2.2.2]- or [3.2.1]bicyclooctyl;

$C_5$–$C_7$-cycloalkanediyl for $R^a$ and $R^b$: a divalent cycloaliphatic radical having 5 to 7 ring carbons, for example cyclopentane-1,2-diyl or -1,3-diyl, cyclohexane-1,2-diyl, -1,3-diyl or -1,4-diyl, cycloheptane-1,2-diyl, -1,3-diyl or -1,4-diyl;

5- to 7-membered heterocyclyl, and heterocyclyl moieties and fused 5- or 6-membered heterocycles on phenyl or pyridyl: a saturated, partially saturated or unsaturated 5-, 6- or 7-membered heterocyclic ring which contains one, two, three or four identical or different heteroatoms selected from the group consisting of oxygen, sulfur and nitrogen and which, in the case of the fused heterocycles, has at least one C=C double bond, i.e., for example, C-bonded 5-membered rings, such as:
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl, pyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-di-oxathiolan-4-yl, 1,2,3-$\Delta^2$-triazolin-4-yl, 1,2,3-$\Delta^2$triazolin-5-yl, 1,2,4-$\Delta^2$-triazolin-3-yl, 1,2,4-$\Delta^2$triazolin-5-yl, 1,2,4-$\Delta^3$-triazolin-3-yl, 1,2,4-$\Delta^3$triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,2,3-triazol-4-yl, 1,2,4-triazol-3-yl, tetrazol-5-yl;

C-bonded 6-membered rings, such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl, pyridin-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin- 2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-3-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-thiazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl, 3,4-dihydropyrimidin-6-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl or 1,2,4,5-tetrazin-3-yl;

N-bonded 5-membered rings, such as:
  tetrahydropyrrol-1-yl, 2,3-dihydro-1-H-pyrrol-1-yl, 2,5-dihydro-1-H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol.-2-yl, 4,5-dihydro-1-H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

N-bonded 6-membered rings, such as:
  piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholinyl), tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and N-bonded cyclic imides, such as:
phthalimide, tetrahydrophthalimide, succinimide, maleimide, glutarimide, 5-oxotriazolin-1-yl, 5-oxo-1,3,4-oxadiazolin-4-yl or 2,4-dioxo-(1H,3H)-pyrimidin-3-yl;
where heterocyclyl may, together with a fused-on phenyl ring or with a $C_3$–$C_6$-carbocycle or with a further 5- or 6-membered heterocycle, form a bicyclic ring system,
where one ring carbon in the heterocycle may be present as carbonyl or thiocarbonyl group,
where the sulfur of the heterocycles mentioned may be oxidized to S=O or S(=O)$_2$.

Unless indicated otherwise, all phenyl rings or heterocyclyl radicals and all phenyl components in phenoxy, phenylalkyl, phenylamino, phenylcarbonyl, phenyloxycarbonyl, phenylaminocarbonyl and N-alkyl-N-phenylaminocarbonyl, and all heterocyclyl components in heterocyclyloxy, heterocyclylalkyl, heterocyclylcarbonyl, heterocyclyloxycarbonyl, heterocyclylcarbonyloxy are preferably unsubstituted or are partially or fully halogenated and/or carry one, two or three substituents selected from the group consisting of nitro, cyano, hydroxyl, $C_1$–$C_4$-alkyl, $C_1$–$C_4$-haloalkyl, $C_1$–$C_4$-alkoxy, $C_1$–$C_4$-haloalkoxy, $C_1$–$C_6$-alkylamino, di-$C_1$–$C_6$-alkylamino, $C_3$–$C_6$-cycloalkylamino, where the alkyl and cycloalkyl groups of the three last-mentioned radicals may be partially or fully halogenated and/or may carry one to three substituents selected from the group consisting of $C_1$–$C_4$-alkoxy and hydroxyl.

For the reaction of the aryl halides II with the compounds III or III' or III", preference is given to those transition metal catalysts whose active metal component comprises at least one platinum metal and in particular a transition metal selected from the group consisting of palladium, platinum, nickel, cobalt, ruthenium and rhodium. Particular preference is given to those catalysts which comprise palladium as metal of group VIII of the Periodic Table of the Elements.

The catalysts, in particular those which comprise platinum, nickel, cobalt, ruthenium and rhodium and in particular palladium as catalytically active metal, can be employed as metals or in the form of customary salts, for example in the form of halogen compounds, such as $PdCl_2$, $NiCl_2$, $CoCl_2$, $RhCl_3 \cdot H_2O$, acetates, such as $Pd(OAc)_2$, $Co(OAc)_2$, acetylacetonates or cyanides, in the known valence states.

Moreover, the catalytically active metals can be employed in the form of metal complexes, for example with tertiary phosphines, as metal alkyl carbonyls, mixed complexes which comprise at least two different ligands, preferably at least one tertiary phosphine and at least one ligand different therefrom, for example CO, or with transition metal salts complexed with tertiary phosphines.

For the process according to the invention, it has been found to be useful for the catalyst system to comprise, in addition to the transition metal of group VIII of the Periodic Table, a tertiary phosphine, where the tertiary phosphine can be added to the reaction mixture separately or together with the transition metal in the form of a transition metal complex.

Suitable phosphine ligands can be represented, for example, by the formulae below:

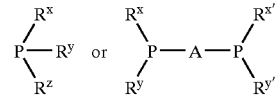

in which A is a divalent organic radical, for example $C_1$–$C_6$—, preferably $C_1$–$C_4$-alkanediyl, in particular 1,2-ethylene or 1,3-propylene, 1,2-cycloalkanediyl, for example 1,2-cyclohexanediyl, 1,2-cyclopentanediyl, ferrocenediyl, a polycyclic aromatic radical, such as 1,8-anthracenediyl, or a 2,2-biphenyl structure.

The radicals $R^x$, $R^y$, $R^{x'}$, $R^{y'}$ are, independently of one another, $C_1$–$C_6$-alkyl, $C_5$–$C_8$-cycloalkyl, such as cyclohexyl, aryl, in particular phenyl or p-tolyl, $C_1$–$C_4$-alkylaryl, for example benzyl, phenethyl, or aryloxy, such as phenoxy. $R^x$, $R^y$, $R^{x'}$, $R^{y'}$ are preferably aryl. Aryl is, for example, phenyl, naphthyl, anthryl, which may be substituted or unsubstituted, and is in particular unsubstituted or substituted phenyl, such as tolyl. With respect to the substituents on aryl, attention has to be paid primarily to their inertness to the reaction conditions used. Suitable radicals are all inert C-organic radicals, such as $C_1$–$C_6$-alkyl radicals, for example methyl, sulfonyl or carboxyl radicals, such as COOH, COOM (M is, for example, an alkali metal, alkaline earth metal or an ammonium salt), or C-organic radicals which are attached via oxygen, such as $C_1$–$C_6$-alkoxy radicals.

Examples of such complexes are $P(C_6H_5)_3$, $P(C_6H_4CH_3)_3$, $P(n-C_4H_9)_3$, $P(cyclo-C_6H_{11})_3$, $PCH_3(C_6H_5)_2$, 1,2-bis(diphenylphosphino)ethane, 1,3-bis(diphenylphosphino)propane, 1,8-bis(diphenylphosphino)anthracene and α,α'-bis(diphenylphosphino)ferrocene. A particularly preferred tertiary phosphine is triarylphosphine and in particular triphenylphosphine, which may be substituted on the phenyl ring.

Examples of complex compounds which are preferred according to the invention are $(PPh_3)_2Ni(CO)_2$, $Pt(CO)_2(PPh_3)_2$, in particular $Pd(CO)(PPh_3)_3$, $(PPh_3)_2Pd(OAc)_2$, $(PPh_3)_2PdCl_2$.

The phosphine complexes can be prepared in a manner known per se. The starting material used is, for example a customary commercially available metal salt, such as $PdCl_2$ or $Pd(OCOCH_3)_2$, and the phosphine, for example $P(C_6H_5)_3$, $P(C_6H_4CH_3)_3$, $P(n-C_4H_9)_3$, $P(cyclo-C_6H_{11})3$, $PCH_3(C_6H_5)_2$, 1,2-bis(diphenylphosphino)ethane, 1,3-bis(diphenylphosphino)propane, 1,8-bis(diphenylphosphino)anthracene or α,α'-bis(diphenylphosphinoferrocene, is added, if appropriate in a solvent. Frequently, the complexes are also generated in situ in the reaction mixture by adding at least one phosphine ligand and a precursor compound, i.e. a transition metal compound which comprises the catalytically active metal, for example a metal salt or another complex of the metal, to the reaction mixture.

If the ligand used in the process according to the invention is a phosphine, the amount of phosphine, based on one mole of transition metal, is at least 0.1 mol, preferably at least 0.5 mol and particularly preferably at least 1 mol. In general, the molar ratio of tertiary phosphine to transition metal will not be above 20, preferably 10 and in particular 5, not least in order to keep the input of foreign substances into reaction components II and III as low as possible.

The catalysts can be employed as such or on a support. The nature of the support is not crucial. Suitable supports include inorganic oxides, such as silicon dioxide, alumina, alumosilicates, for example zeolites, calcium carbonate, barium sulfate, furthermore activated carbon, carbon black. Suitable support materials are furthermore organic polymers, in particular those which are capable of complexing the transition metal, for example polymers having tertiary amino groups, pyridine groups, imidazole groups or polymers having tertiary phosphine groups.

The amount of transition metal is not critical. Obviously, for cost reasons, the use of a small amount, for example from 0.1 to 20 mol %, in particular from 0.5 to 10 mol %, based on the aryl halide II, will be preferred. It is, of course, also possible to use relatively large amounts, for example 50, 100 or 200 mol %, based on 1 mole of aryl halide II.

Suitable for the process according to the invention are all inert bases capable of binding the hydrogen halide, in particular hydrogen bromide, released during the reaction. Examples of suitable bases are amines, preferably tertiary amines, in particular trialkylamines, such as triethylamine, triethanolamine, cyclic amines, such as N-methylpiperidine, triethylenediamine(=1,4-diazabicyclo[2.2.2]octane), 1,5-diazabicyclo[4.3.0]non-5-ene, 1,8-diazabicyclo[5.4.0]undec-7-ene or N,N'-dimethylpiperazine, heteroaromatic amines, such as pyridine and substituted pyridines, furthermore alkali metal carbonates or bicarbonates, or tetraalkyl-substituted urea derivatives, such as tetra-$C_1$–$C_4$-alkylurea, for example tetramethylurea.

The amount of base is not critical; usually, the base will be employed in an amount of at least one mole per mole of aryl halide II, for example in an amount of from 1 to 10 mole, in particular from 1 to 5 mole. It is, of course, also possible to use the base as solvent or diluent for the reactants. If the base is simultaneously used as solvent, the amount is generally such that the reaction partners are dissolved, unnecessarily high excesses being avoided for reasons of practicability in order to save costs, to be able to employ small reaction vessels and to ensure that the reaction partners have maximum contact.

However, depending on the nature of the starting materials and the catalyst used, it may be advantageous to use an inert solvent different from the reaction partner or the base.

Suitable inert solvents are, for example, aromatic hydrocarbons, such as toluene, xylenes, cumene, aliphatic hydrocarbons, such as hexane, pentane or cyclohexane, halogenated aliphatic hydrocarbons, such as dichloromethane, trichloromethane, carbon tetrachloride, 1,2-dichloroethane and 1,1-dichloroethane, ethers, such as methyl tert-butyl ether, tetrahydrofuran, dioxane, dimethoxyethane, substituted amides, such as dimethylformamide or N-methylpyrrolidone, persubstituted ureas, such as tetra-$C_1$–$C_4$-alkylureas, or nitriles, such as benzonitrile or acetonitrile, and also mixtures of the solvents mentioned above. Preferred solvents are aromatic hydrocarbons or solvent mixtures containing a high proportion of aromatic hydrocarbons.

Furthermore, it is found to be useful to carry out the process according to the invention in the presence of lithium ions. Suitable sources of lithium are, in particular, lithium salts, such as lithium halides, for example lithium chloride, furthermore basic lithium salts, such as lithium carbonate, lithium acetate or lithium hydroxide. In these preferred embodiments of the process according to the invention, in general from 0.1 to 10 mol, in particular from 0.2 to 5 mol and particularly preferably from 0.5 to 2 mol of lithium ions are employed per mole of aryl halide.

In the process according to the invention, aryl halide II and the compounds III or III' or III" are generally employed in approximately stoichiometric amounts, an excess of one of the components of up to 50 mol %, based on the component which is present in substoichiometric amounts, generally not having any negative effect. The diketone III or its tautomer III' or III" is preferably employed in an approximately equimolar amount, or in excess.

During the reaction, the carbon monoxide pressure is adjusted such that there is always an excess of carbon monoxide, based on the aryl halide. The carbon monoxide partial pressure at room temperature is preferably from 1 to 250 bar, in particular from 5 to 150 bar, CO.

The process according to the invention is generally carried out at temperatures of from room temperature to 300° C., preferably at 50–250° C., in particular at 100–200° C., continuously or batchwise. If the process is carried out batchwise, it is expedient, in order to maintain a constant pressure, to continuously introduce pressurized carbon monoxide into the reaction mixture.

The process according to the invention can be applied to a large number of different substrate compounds II and III. In the formula II, Hal is preferably bromine or iodine and in particular bromine.

Aryl halides II which may be mentioned are, for example, compounds which are represented by the formula IIa

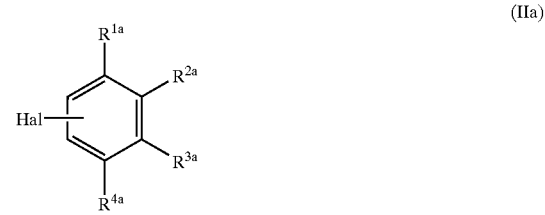

in which Hal is chlorine, bromine or iodine, preferably bromine or iodine and in particular bromine and Hal is preferably adjacent to the radical $R^{1a}$, and $R^{1a}$ and $R^{4a}$ independently of one another are hydrogen, halogen, in particular fluorine, chlorine, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, hydroxy-$C_1$–$C_6$-alkyl, $C_1$–$C_6$-alkylsulfonyl, $C_1$–$C_6$-haloalkylsulfonyl, $C_1$–$C_6$-alkoxy-$C_1$–$C_6$-alkyl, $C_1$–$C_6$-alkylthio-$C_1$–$C_6$-alkyl, $C_1$–$C_6$-haloalkylthio-$C_1$–$C_6$-alkyl, $C_1$–$C_6$-alkylsulfonyl-$C_1$–$C_6$-alkyl, $C_1$–$C_6$-haloalkylsulfonyl-$C_1$–$C_6$-alkyl, $C_1$–$C_6$-alkylamino-$C_1$–$C_6$-alkyl, or di($C_1$–$C_6$-alkyl)amino-$C_1$–$C_6$-alkyl and $R^{2a}$ and $R^{3a}$ form a 5- or 6-membered saturated or unsaturated heterocycle which may have 1, 2 or 3 heteroatoms selected from the group consisting of N, S and O, where sulfur atoms in the heterocycle may also be present as sulfoxide or sulfone, nitrogen atoms and carbon atoms in the heterocycle have a hydrogen atom or a substituent selected from the group consisting of halogen, nitro, cyano, hydroxy, amino, $C_1$–$C_6$-alkyl, $C_1$–$C_6$-haloalkyl, $C_1$–$C_6$-aminoalkyl, hydroxy-$C_1$–$C_6$-alkyl $C_1$–$C_6$-alkylcarbonyl, $C_1$–$C_6$-alkylcarbonyloxy, $C_1$–$C_6$-alkyloxycarbonyl, $C_1$–$C_6$-alkoxy-$C_1$–$C_6$-alkyl, $C_1$–$C_6$-alkylcarbonyl-$C_1$–$C_6$-alkyl, $C_1$–$C_6$-alkoxy, $C_1$–$C_6$-haloalkoxy, $C_2$–$C_6$-alkenyl, $C_2$–$C_6$-alkynyl, $C_1$–$C_6$-hydroxyalkoxy, $C_1$–$C_6$-alkoxy-$C_1$–$C_6$-alkoxy, $C_3$–$C_6$-cycloalkyl, $C_3$–$C_8$-cycloalkoxy, $C_1$–$C_6$-alkylthio, $C_1$–$C_6$-haloalkylthio, $C_1$–$C_6$-hydroxyalkylthio, $C_1$–$C_6$-alkoxy-$C_1$–$C_6$-alkylthio, phenyl, phenyl-$C_1$–$C_6$-alkyl, phenylcarbonyl, phenylcarbonyloxy, phenoxycarbonyl, 5-, 6- or 7-membered heterocyclyl, phenoxy, phenylamino, diphenylamino, heterocyclyl-$C_1$-$C_6$-alkyl, heterocyclyloxy, heterocyclylcarbonyl, heterocyclyloxycarbonyl, heterocyclylcarbonyloxy, where the phenyl and heterocyclyl groups of the 14 last-mentioned radicals may for their part be partially of fully halogenated and/or may carry one, two or three substituents selected from the group consisting of nitro, cyano, hydroxyl, $C_1$-$C_4$-alkyl, $C_1$-$C_4$-haloalkyl, $C_1$-$C_4$-alkoxy and $C_1$-$C_4$-haloalkoxy, $C_1$-$C_6$-alkylamino, di-$C_1$-$C_6$-alkylamino, $C_3$-$C_6$-cycloalkylamino, where the alkyl and cycloalkyl groups of the three last-mentioned radicals may be partially or fully halogenated and/or may carry one to three substituents selected from the group consisting of $C_1$-$C_4$-alkoxy or hydroxyl, where carbon ring members may also be present as carbonyl function, thiocarbonyl function, oxime or oxime ether function; or $R^{1a}$ and $R^{2a}$ or $R^{3a}$ and $R^{4a}$ form a fused 5- or 6-membered saturated or unsaturated heterocycle which may have 1, 2 or 3 heteroatoms selected from the group consisting of N, S and O, where the ring atoms of the heterocycle may be substituted in the manner described above; and the remaining radicals $R^{1a}$, $R^{2a}$, $R^{3a}$ and $R^{4a}$ independently of one another have the meanings mentioned for $R^{1a}$, or $R^{2a}$ is hydrogen or fused 5-, 6- or 7-membered heterocyclyl which has 1, 2 or 3 hetero atoms selected from the group consisting of N, S and O, where the ring atoms of the heterocycle may be substituted in the manner described above; and $R^{1a}$, $R^{3a}$ and $R^{4a}$ independently of one another have the meanings mentioned above for $R^{1a}$.

Fused 5- or 6-membered heterocycles which may be mentioned are, for example, pyrrole, 2,3-dihydropyrrole, 2,5-dihydropyrrole, pyrazole, 2,3-dihydropyrazole, imidazole, 2,3-dihydroimidazole, triazole, furan, 2,3- and 2,5-dihydrofuran, oxazole, 2,3-dihydrooxazole, isoxazole, 2,3-dihydroisoxazole, thiophene, 2,3- and 2,5-dihydrothiophene, thiazol, 2,3-dihydrothiazole, isothiazole, 2,3-dihydroisothiazole, pyridine, 1,2-, 2,3- and 3,4-dihydropyrimidine and tetrahydropyridine. Fused carbocycles are, for example, cyclopentene, cyclopentadiene, cyclohexene, cyclohexadiene, benzene, cycloheptene.

Thus, for example, $R^{1a}$ and $R^{2a}$ or $R^{3a}$ and $R^{4a}$ form, together with the benzene ring to which they are attached, an indole, isoindole, benzofuran, isobenzofuran, benzo-[a]-thiophene benzo-[b]-thiophene, benzimidazole, benzoxazole, benzothiazole, benzisothiazole, benzotriazole, quinoline, isoquinoline, quinoxaline, chromane, thiochromane, chromene, thiochromen, indane, indene or naphthalene ring, or a derivative thereof which is partially hydrogenated on the fused ring.

The heterocyclic structures may, of course, also be partially hydrogenated, and the N and/or C ring atoms may be substituted in the manner described above. Carbon ring members can also be present as carbonyl function, thiocarbonyl function, oxime or oxime-ether function, as in chroman-4-one, thiochroman-4-one, benzoisothiazolone, and ring sulfur atoms may be present as sulfoxide or sulfone, such as benzothiophene S-oxide, benzothiophene S,S-dioxide, benzothiazole S-oxide, benzothiazole S,S-dioxide, thiochromane S-oxide and thiochromane S,S-dioxide.

In a preferred embodiment of the process according to the invention, aryl halides of the formula IIb are employed:

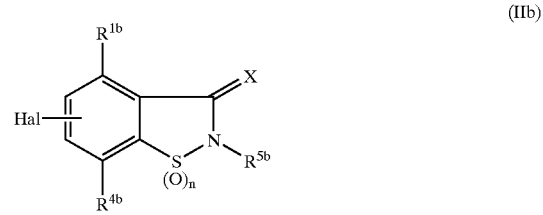

(IIb)

in which Hal is as defined above and $R^{1b}$ and $R^{4b}$ have the meanings give above for $R^{1a}$ and $R^{4a}$, respectively, Hal is preferably adjacent to $R^{1b}$, $R^{1b}$ is preferably halogen, in particular fluorine or chlorine, $C_1$-$C_4$-alkyl, $C_1$-$C_4$-haloalkyl, $C_1$-$C_4$-alkoxy and $C_1$-$C_4$-haloalkoxy, $R^{4b}$ is preferably hydrogen, fluorine, chlorine, methyl or methoxy, $R^{5b}$ is hydrogen, $C_1$-$C_6$-alkyl, $C_1$-$C_6$-haloalkyl, $C_1$-$C_6$-alkylcarbonyl, $C_1$-$C_6$-alkoxy-$C_1$-$C_6$-alkyl, $C_2$-$C_6$-alkenyl, $C_2$-$C_6$-alkynyl, $C_1$-$C_6$-hydroxyalkoxy, $C_1$-$C_6$-alkoxy-$C_1$-$C_6$-alkoxy, $C_3$-$C_8$-cycloalkyl, phenyl, phenyl-$C_1$-$C_6$-alkyl, where phenyl in the two last-mentioned groups may carry one, two or three substituents selected from the group consisting of halogen, nitro, cyano, hydroxyl, $C_1$-$C_4$-alkyl, $C_1$-$C_4$-haloalkyl, $C_1$-$C_4$-alkoxy and $C_1$-$C_4$-haloalkoxy, and is in particular $C_1$-$C_4$-alkyl, phenyl or phenyl-$C_1$-$C_4$-alkyl, where phenyl may be unsubstituted or substituted in the manner described above.

n is 0, 1 or 2 and

X is oxygen or sulfur, in particular oxygen.

In a further preferred embodiment of the process according to the invention, aryl halides of the formula IIc are employed

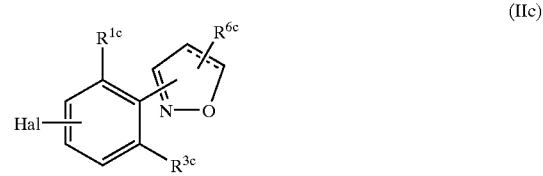

(IIc)

in which Hal is as defined above and is preferably adjacent to $R^{1c}$, $R^{1c}$ has the meanings given for $R^{1a}$ and is preferably halogen, in particular fluorine or chlorine, $C_1$-$C_4$-alkyl, in particular methyl, $C_1$-$C_4$-haloalkyl, $C_1$-$C_4$-alkoxy and $C_1$-$C_4$-haloalkoxy, $R^{3c}$ is halogen, $C_1$-$C_6$-alkyl, $C_1$-$C_6$-haloalkyl, $C_1$-$C_6$-alkylthio, $C_1$-$C_6$-alkylsulfinyl, $C_1$-$C_6$-alkylsulfonyl, $C_1$-$C_6$-alkoxy or $C_1$-$C_6$-haloalkoxy, and in particular $C_1$-$C_6$-alkylsulfonyl and especially chlorine, fluorine, methyl, methoxy or methylsulfonyl, === is a double bond or preferably a single bond and $R^{6c}$ is hydrogen or unsubstituted or substituted $C_1$-$C_4$-alkyl. In this context, substituted $C_1$-$C_4$-alkyl is preferably haloalkyl as defined above, for example fluoromethyl, chloromethyl, difluoromethyl, chlorodifluoromethyl or trifluoromethyl, or $C_1$-$C_4$-alkoxy-$C_1$-$C_4$-alkyl as defined above, for example methoxymethyl.

In a further preferred embodiment of the process according to the invention, aryl halides of the formula IId are employed

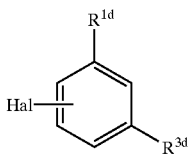

(IId)

in which Hal is as defined above and is preferably adjacent to $R^{1d}$, $R^{1d}$ has the meanings mentioned for $R^{1a}$ and is preferably halogen, and in particular fluorine or chlorine, $C_1$–$C_4$-alkyl, in particular methyl, $C_1$–$C_4$-haloalkyl, $C_1$–$C_4$-alkoxy and $C_1$–$C_4$-haloalkoxy, $R^{3d}$ is halogen, $C_1$–$C_6$-alkyl, $C_1$–$C_6$-haloalkyl, $C_1$–$C_6$-alkylthio, $C_1$–$C_6$-alkylsulfinyl, $C_1$–$C_6$-alkylsulfonyl, $C_1$–$C_6$-alkoxy or $C_1$–$C_6$-haloalkoxy and in particular $C_1$–$C_6$-alkylsulfonyl and especially chlorine, fluorine, methyl, methoxy or methylsulfonyl.

The compound II used in the process according to the invention may, of course, also be an unsubstituted halobenzene, such as bromobenzene, or a halopyridine, such as 2-, 3- or 4-bromopyridine.

The 1,3-diketone of the formula III (or the tautomer III' or III") used in the process according to the invention is preferably a cyclic or bicyclic 1,3-diketone of the formula IIIa or IIIb:

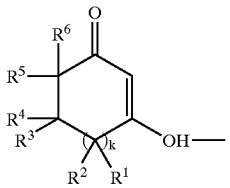

(IIIa)

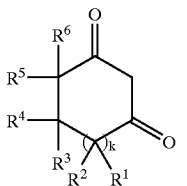

(IIIb)

in which k is 0, 1 or 2 and the variables $R^1$ to $R^6$ as defined below:

$R^1$, $R^5$ independently of one another are hydrogen, $C_1$–$C_4$-alkyl, in particular methyl, or $C_1$–$C_4$-alkoxycarbonyl;

$R^2$, $R^4$, $R^6$ independently of one another are hydrogen, $C_1$–$C_4$-alkyl, in particular methyl, $C_1$–$C_4$-alkoxy such as methoxy or $C_1$–$C_4$-alkylthio such as methylthio;

$R^3$ is hydrogen, halogen, hydroxyl, $C_1$–$C_6$-alkyl, $C_1$–$C_6$-haloalkyl, di($C_1$–$C_6$-alkoxy)methyl, ($C_1$–$C_6$-alkoxy)-($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkoxycarbonyl, $C_1$–$C_6$-haloalkoxycarbonyl; in particular, hydrogen or methyl 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last-mentioned radicals may be substituted by one to three $C_1$–$C_4$-alkyl radicals; or $R^2$ and $R^4$ or $R^4$ and $R^6$ together form a π bond or a $C_1$–$C_5$-alkanediyl chain which may have a π bond and/or may carry one, two or three radicals from the following group: halogen, cyano, $C_1$–$C_4$-alkyl, $C_1$–$C_4$-haloalkyl or $C_1$–$C_4$-alkoxycarbonyl; or $R^5$ and $R^6$ together form a $C_1$–$C_5$-alkanediyl chain which may have a π bond and/or may carry one, two or three radicals from the following group: halogen, cyano, $C_1$–$C_4$-alkyl, $C_1$–$C_4$-haloalkyl or $C_1$–$C_4$-alkoxycarbonyl; or $R^2$ and $R^6$ together form a $C_1$–$C_4$-alkanediyl chain which may have a π bond and/or may carry one, two or three radicals from the following group: halogen, cyano, $C_1$–$C_4$-alkyl, $C_1$–$C_4$-haloalkyl or $C_1$–$C_4$-alkoxycarbonyl, which is preferably unsubstituted; or $R^3$ and $R^4$ together form a chain of the formula —O—$(CH_2)_p$—O—, —O—$(CH_2)_p$—S—, —S—$(CH_2)_p$—S—, —O—$(CH_2)_q$— or —S—$(CH_2)_q$—, in which p is 2, 3, 4 or 5 preferably 2 or 3 and q is 2, 3, 4, 5 or 6 and which may be substituted by one, two or three radicals from the following group: halogen, cyano, $C_1$–$C_4$-alkyl, $C_1$–$C_4$-haloalkyl or $C_1$–$C_4$-alkoxycarbonyl and is preferably unsubstituted; or $R^3$ and $R^4$ together with the carbon to which they are attached form a carbonyl or thiocarbonyl group.

Examples of preferred cyclic diketones of the formula IIIa or IIIb are the cyclohexane 1,3-diones of the formulae III-1 to III-12:

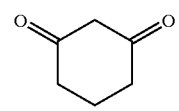

(III-1)

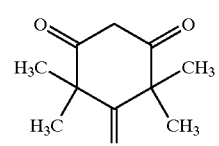

(III-2)

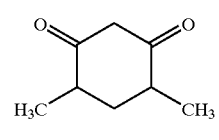

(III-3)

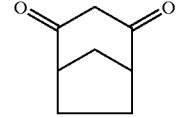

(III-4)

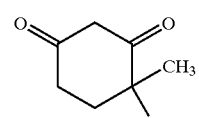

(III-5)

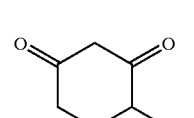

(III-6)

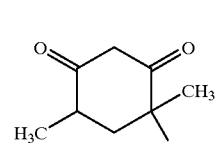

(III-7)

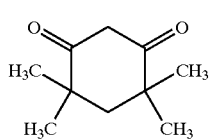 (III-8)

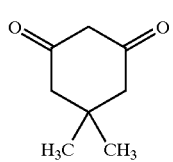 (III-9)

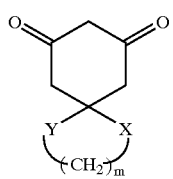 (III-10)

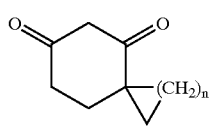 (III-11)

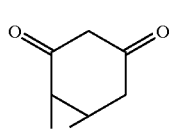 (III-12)

Y = X = O or S
n = 1, 2, 3 or 4
m = 2, 3 or 4

Work-up of the reaction according to the invention of aryl halide II with 1,3-diketone III can be carried out in a manner known per se. The reaction mixture can, for example, be evaporated to dryness, preferably under reduced pressure. In general, the residue is then recrystallized from a suitable solvent and/or purified chromatographically, where the solvent used for recrystallization and the stationary phase and the mobile phase (eluent) used for chromatography do, of course, depend on the nature of the starting material and can be determined in a simple manner by a person skilled in the art using standard tests. In many cases, silica or alumina is a suitable stationary phase. Suitable eluents are, for example, aliphatic and cycloaliphatic hydrocarbons, such as n-hexane or cyclohexane, or mixtures thereof with polar solvents, such as ethers, or esters, for example ethyl acetate. It is, of course, also possible to work-up the reaction mixture by aqueous extraction, to remove salts, for example acid addition salts formed during the reaction, of hydrogen halide and the base that is employed, or catalysts.

The process according to the invention affords the β-ketoenol esters of the formula I in good yields. The great advantage of the process is in particular the fact that, in place of the aryl carboxylic acids AR—COOH, some of which are difficult to prepare, it is possible to use the aryl halides of the formula II, which are easier to obtain.

The β-Ketoenol esters of the formula I which can be obtained by the process according to the invention are generally rearranged in a subsequent reaction by treatment of I with a base and a catalytically effective amount of at least one cyanide compound, to give the 2-aryl-substituted 1,3-diketones of the formula X. To this end, the β-Ketoenol esters I can be used as isolated pure substance, as isolated crude product of the reaction described above or in the reaction mixture of the reaction described above, without prior isolation. The reaction mixture obtained by the process according to the invention can, for example, be admixed directly, after removal of the carbon monoxide, with a base and a catalytically effective amount of at least one cyanide compound, whereby the rearrangement of I into the compound X is initiated.

Rearrangement of the β-ketoenol esters I into the compounds of the formula X is generally carried out at 20–100° C. in a solvent and in the presence of a base and, if appropriate, using a cyano compound as catalyst.

Suitable for use as solvents are, for example, acetonitrile, methylene chloride, 1,2-dichloroethane, dioxane, ethyl acetate, toluene or mixtures of these. Preferred solvents are acetonitrile and dioxane, and mixtures thereof.

Suitable bases are the tertiary amines mentioned above, such as triethylamine and pyridine, alkaline earth metal or alkali metal carbonates, such as sodium carbonate or potassium carbonate, which are preferably employed in an equimolar amount or an up to four-fold excess, based on the β-Ketoenol ester of the formula I. Preference is given to using triethylamine or alkali metal carbonate, preferably in twice the equimolar ratio, based on the ester.

Suitable for use as cyano compounds are, for example, inorganic cyanides, such as sodium cyanide or potassium cyanide, and organic cyano compounds which can release cyanide ions, for example cyanohydrins of aliphatic ketones, which is acetone-cyanohydrin, or trialkylsilyl cyanides, such as trimethylsilyl cyanide. They are preferably employed in an amount of from 1 to 50 mol percent, in particular 5 to 25 mol %, based on the β-ketoenol ester I. Preference is given to using acetone cyanohydrin or trimethylsilyl cyanide, for example in an amount of from 5 to 25, preferably about 10 to 20, mol percent, based on the β-ketoenol ester I.

Work-up can be carried out in a manner known per se. The reaction mixture of the rearrangement is, for example, acidified with dilute mineral acid, for example 5% strength hydrochloric acid or sulfuric acid, and extracted with an organic solvent, for example methylene chloride or ethyl acetate. To remove impurities, the organic extract can be extracted with a base, such as 5–10% strength alkali metal carbonate solution, for example sodium carbonate or potassium carbonate solution. The aqueous phase is acidified and the resulting precipitate is filtered off with suction and/or extracted with methylene chloride or ethyl acetate, the extract being dried and concentrated. If appropriate, the residue is recrystallized and/or further purified chromatographically, in the manner described above.

The examples below serve to illustrate the invention in more detail.

I. β-Ketonenol ester

General procedure for the reaction of 5-bromo-2,4-dimethylsaccharin (5-bromo-2,4-dimethyl-1,2-benzoisothiazol-3(2H)-one 1,1-dioxide=compound of the formula IIb where $R^{1b}=R^{5b}$=methyl, $R^{4b}$=hydrogen, X=0, n=2 and Hal=bromine) with cyclohexan-1,3-dionenes of the formula IIIa in a laboratory autoclave (Examples 1 to 3).

1 g (3.6 mmol) of 5-bromo-2,4-dimethylsaccharin, 4.3 mmol (1.2 eq.) of 1,3-diketone, 0.1 g of bis (triphenylphosphine)palladium dichloride, 0.15 g (3.6 mmol) of lithium chloride and 0.73 g (7.2 mmol) of triethylamine were initially charged in 100 ml of solvent in a laboratory autoclave. The gas space of the autoclave was then flushed 1 to 6 times with carbon monoxide, the autoclave was heated to 140° C. and a carbon monoxide pressure of 20 bar was then applied. Temperature and pressure were maintained for 12 to 24 h, and the autoclave was then cooled and vented to atmospheric pressure and the reaction mixture was concentrated to dryness.

For work-up according to Method A, the residue was chromatographed on silica gel using a cyclohexane/ethyl acetate gradient (100/0 to 60/40 v/v).

For work-up according to method B, the residue was taken up in ethyl acetate and washed three times with 5% by weight strength aqueous sodium carbonate, twice with 10% by weight strength hydrochloric acid and twice with water. The organic phase was dried over sodium carbonate and concentrated to dryness under reduced pressure.

In each case, the respective β-ketoenol ester of 2,4-dimethylsaccharin-5-carboxylic acid was obtained as a viscous oil or as a white solid.

The authenticity of the resulting compounds was checked by $^1$H-NMR spectrum. The starting materials and results of the reaction are given in Table 1.

TABLE 1

| Example | Diketone | Solvent | Work-up | Yield [%][1] |
|---------|----------|---------|---------|--------------|
| 1 | III-9 | Toluene | A | 17.6 |
| 2 | III-4 | Toluene | B | 77.7 |
| 3 | III-4 | Dioxane | B | 63 |

[1]Based on 5-bromo-2,4-dimethylsaccharine

EXAMPLE 4

10 g (36 mmol) of 5-bromo-2,4-dimethylsaccharine, 5 g (36 mmol) of bicyclo[3.2.1]-1,3-dioxooctane (diketone III-4), 1 g of bis(triphenylphosphine)palladium dichloride, 1.5 g (3.6 mmol) of lithium chloride and 7.3 g (72 mmol) of triethylamine were initially charged in 700 ml of toluene in a 1-1-autoclave and inertized. The gas space of the autoclave was then flushed with carbon monoxide, the autoclave was heated to 140° C. and a carbon monoxide pressure of 20 bar was applied. Temperature and pressure were maintained for 24 h, and the autoclave was then cooled and vented to atmospheric pressure.

For work-up, the reaction mixture was washed 3 times each with 5% by weight strength aqueous sodium carbonate, 10% by weight strength hydrochloric acid and water. The organic phase was dried over sodium sulfate and evaporated to dryness under reduced pressure. This gave 10.4 g of 5-[(bicyclo[3.2.1]-3-oxoocten-1-yl)oxycarbonyl]-2,4-dimethylsaccharin as a viscous oil.

EXAMPLE 5

In the presence of bis(triphenylphosphine)palladium dichloride, lithium chloride and triethylamine, 1-bromo-2,4-dichlorobenzene and 4,4,6,6-tetramethyl-1,3,5-trioxocyclohexane (diketone III-2) were reacted in the manner and the ratios described for Example 4. This gave, after work-up, (4,4,6,6-tetramethyl-3,5-dioxo-cyclohexen-1-yl)-2,4-dichloro-benzoate in a yield of 30%.

EXAMPLE 6

In the presence of bis(triphenylphosphine)palladium dichloride, lithium chloride and triethylamine, 1-bromo-2,4-dichlorobenzene and 4,6-dimethyl-1,3-dioxocyclohexane (diketone III-3) were reacted in the manner and the ratios described for Example 4. This gave, after work-up, (4,6-dimethyl-3-dioxocyclohex-1-ene-1-yl)-2,4-dichlorobenzoate in a yield of 27%.

EXAMPLE 8

In the presence of bis(triphenylphosphine)palladium dichloride, lithium chloride and triethylamine, 1-bromo-2-methyl-4-methylsulfonyl-3-(4'-5'-dihydrooxazol-3-yl)benzene and (36 mmol) 5,5-dimethyl-1,3-dioxocyclohexan (diketone III-9) were reacted in the manner and the ratios described for example 4. This gave, after work-up, 1-(5,5-dimethyl-3-oxocyclohex-1-en-1-yl)oxycarbonyl-2-methyl-4-methylsulfonyl-3-(4',5'-dihydrooxazol-3-yl)benzene in a yield of 35%.

EXAMPLE 9

In the presence of bis(triphenylphosphine)palladium dichloride, lithium chloride and triethylamine, 1-bromo-2-methyl-4-methylsulfonyl-3-(4'-5'-dihydrooxazol-3-yl)benzene and cyclohexan-1,3-dione (diketone III-1) were reacted in the manner and the ratios described for Example 4. This gave, after work-up, 1-(3-oxocyclohex-1-en-1-yl)oxycarbonyl-2-methyl-4-methylsulfonyl-3-(4',5'-dihydrooxazol-3-yl)benzene.

In the manner descried in Examples 8 and 9, it is furthermore possible to prepare the β-ketoenol esters of the formula below

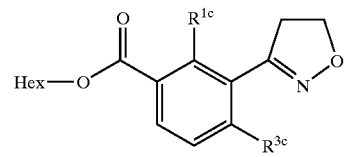

where Hex, $R^{1c}$ and $R^{3c}$ are each as defined in Table 2. Hex is one of the cyclohexenone radicals Hex-1 to Hex-5 defined below

(Hex-1)

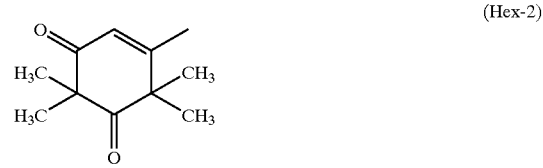
(Hex-2)

(Hex-3)

(Hex-4)

(Hex-5)

TABLE 2

| Example | Hex | $R^{1c}$ | $R^{3c}$ |
|---|---|---|---|
| 8 | Hex-5 | $CH_3$ | $SO_2CH_3$ |
| 9 | Hex-1 | $CH_3$ | $SO_2CH_3$ |
| 10 | Hex-5 | F | Cl |
| 11 | Hex-5 | F | F |
| 12 | Hex-5 | F | $OCH_3$ |
| 13 | Hex-5 | F | $CH_3$ |
| 14 | Hex-5 | F | $SO_2CH_3$ |
| 15 | Hex-5 | $CH_3$ | Cl |
| 16 | Hex-5 | $CH_3$ | F |
| 17 | Hex-5 | $CH_3$ | $OCH_3$ |
| 18 | Hex-5 | $CH_3$ | $CH_3$ |
| 19 | Hex-5 | $OCH_3$ | Cl |
| 20 | Hex-5 | $OCH_3$ | F |
| 21 | Hex-5 | $OCH_3$ | $OCH_3$ |
| 22 | Hex-5 | $OCH_3$ | $CH_3$ |
| 23 | Hex-5 | $OCH_3$ | $SO_2CH_3$ |
| 24 | Hex-5 | Cl | Cl |
| 25 | Hex-5 | Cl | F |
| 26 | Hex-5 | Cl | $OCH_3$ |
| 27 | Hex-5 | Cl | $CH_3$ |
| 28 | Hex-5 | Cl | $SO_2CH_3$ |
| 29 | Hex-1 | F | Cl |
| 30 | Hex-1 | F | F |
| 31 | Hex-1 | F | $OCH_3$ |
| 32 | Hex-1 | F | $CH_3$ |
| 33 | Hex-1 | F | $SO_2CH_3$ |
| 34 | Hex-1 | $CH_3$ | Cl |
| 35 | Hex-1 | $CH_3$ | F |
| 36 | Hex-1 | $CH_3$ | $OCH_3$ |
| 37 | Hex-1 | $CH_3$ | $CH_3$ |
| 38 | Hex-1 | $OCH_3$ | Cl |
| 39 | Hex-1 | $OCH_3$ | F |
| 40 | Hex-1 | $OCH_3$ | $OCH_3$ |
| 41 | Hex-1 | $OCH_3$ | $CH_3$ |
| 42 | Hex-1 | $OCH_3$ | $SO_2CH_3$ |
| 43 | Hex-1 | Cl | Cl |
| 44 | Hex-1 | Cl | F |
| 45 | Hex-1 | Cl | $OCH_3$ |
| 46 | Hex-1 | Cl | $CH_3$ |
| 47 | Hex-1 | Cl | $SO_2CH_3$ |
| 48 | Hex-2 | F | Cl |
| 49 | Hex-2 | F | F |
| 50 | Hex-2 | F | $OCH_3$ |
| 51 | Hex-2 | F | $CH_3$ |
| 52 | Hex-2 | F | $SO_2CH_3$ |
| 53 | Hex-2 | $CH_3$ | Cl |
| 54 | Hex-2 | $CH_3$ | F |
| 55 | Hex-2 | $CH_3$ | $OCH_3$ |
| 56 | Hex-2 | $CH_3$ | $CH_3$ |
| 57 | Hex-2 | $CH_3$ | $SO_2CH_3$ |
| 58 | Hex-2 | $OCH_3$ | Cl |
| 59 | Hex-2 | $OCH_3$ | F |
| 60 | Hex-2 | $OCH_3$ | $OCH_3$ |
| 61 | Hex-2 | $OCH_3$ | $CH_3$ |
| 62 | Hex-2 | $OCH_3$ | $SO_2CH_3$ |
| 63 | Hex-2 | Cl | Cl |
| 64 | Hex-2 | Cl | F |
| 65 | Hex-2 | Cl | $OCH_3$ |
| 66 | Hex-2 | Cl | $CH_3$ |
| 67 | Hex-2 | Cl | $SO_2CH_3$ |
| 68 | Hex-3 | F | Cl |
| 69 | Hex-3 | F | F |
| 70 | Hex-3 | F | $OCH_3$ |
| 71 | Hex-3 | F | $CH_3$ |
| 72 | Hex-3 | F | $SO_2CH_3$ |
| 73 | Hex-3 | $CH_3$ | Cl |
| 74 | Hex-3 | $CH_3$ | F |
| 75 | Hex-3 | $CH_3$ | $OCH_3$ |
| 76 | Hex-3 | $CH_3$ | $CH_3$ |
| 77 | Hex-3 | $CH_3$ | $SO_2CH_3$ |
| 78 | Hex-3 | $OCH_3$ | Cl |
| 79 | Hex-3 | $OCH_3$ | F |
| 80 | Hex-3 | $OCH_3$ | $OCH_3$ |
| 81 | Hex-3 | $OCH_3$ | $CH_3$ |
| 82 | Hex-3 | $OCH_3$ | $SO_2CH_3$ |
| 83 | Hex-3 | Cl | Cl |
| 84 | Hex-3 | Cl | F |
| 85 | Hex-3 | Cl | $OCH_3$ |
| 86 | Hex-3 | Cl | $CH_3$ |
| 87 | Hex-3 | Cl | $SO_2CH_3$ |
| 88 | Hex-4 | F | Cl |
| 89 | Hex-4 | F | F |
| 90 | Hex-4 | F | $OCH_3$ |
| 91 | Hex-4 | F | $CH_3$ |
| 92 | Hex-4 | F | $SO_2CH_3$ |
| 93 | Hex-4 | $CH_3$ | Cl |
| 94 | Hex-4 | $CH_3$ | F |
| 95 | Hex-4 | $CH_3$ | $OCH_3$ |
| 96 | Hex-4 | $CH_3$ | $CH_3$ |
| 97 | Hex-4 | $CH_3$ | $SO_2CH_3$ |
| 98 | Hex-4 | $OCH_3$ | Cl |
| 99 | Hex-4 | $OCH_3$ | F |
| 100 | Hex-4 | $OCH_3$ | $OCH_3$ |
| 101 | Hex-4 | $OCH_3$ | $CH_3$ |
| 102 | Hex-4 | $OCH_3$ | $SO_2CH_3$ |
| 103 | Hex-4 | Cl | Cl |
| 104 | Hex-4 | Cl | F |
| 105 | Hex-4 | Cl | $OCH_3$ |
| 106 | Hex-4 | Cl | $CH_3$ |
| 107 | Hex-4 | Cl | $SO_2CH_3$ |

II. 2-Aroyl-1,3-diketones

The rearrangement of the compounds prepared under I can be carried out, for example, according to Example C) 17, p. 19 of WO 96/05182, which is expressly incorporated herein by way of reference.

We claim:

1. A process for preparing β-ketoenol esters of the formula Ia or Ib

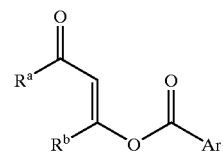

(Ia)

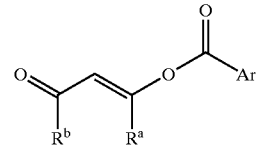

(Ib)

in which $R^a$, $R^b$ independently of one another are $C_1$–$C_6$-alkyl or $C_3$–$C_8$-cycloalkyl, or $R^a$ and $R^b$ together are $C_2$–$C_4$-alkanediyl or $C_5$–$C_7$-cycloalkanediyl, where the three groups mentioned above may be substituted or unsubstituted and may have a fused 3-, 4-, 5- or 6-membered saturated carbocycle, a spiro-linked 3-, 4-, 5- or 6- or 7-membered saturated carbocycle, a spiro-linked 3-, 4-, 5-, 6- or 7-membered saturated heterocycle having 1 or 2 chalkogen atoms, selected from the group consisting of oxygen and sulfur and/or a carbonyl or thiocarbonyl group;

Ar is phenyl or pyridyl, which may in each case have 1, 2, 3 or 4 substituents, it also being possible for two substituents attached to adjacent carbon atoms to form, together with these atoms, a 5- or 6-membered saturated or unsaturated carbocycle or a 5- or 6-membered saturated or unsaturated heterocycle which has 1, 2 or 3 hetero atoms selected from the group consisting of O, N and S and which for its part may be substituted or unsubstituted;

which comprises reacting an aryl halide of the formula II $$Ar\text{-}Hal \qquad (II)$$

in which Hal is bromine with a 1,3-diketone of the formula III or its tautomer III' or III''

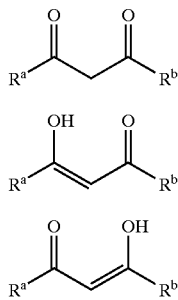

in a carbon monoxide atmosphere in the presence of a base and a catalyst which comprises at least one transition metal of group VIII of the Periodic Table of the Elements.

2. A process as claimed in claim 1, wherein the catalyst comprises the transition metal palladium.

3. A process as claimed in claim 1, wherein the catalyst additionally comprises a tertiary phosphine.

4. A process as claimed in claim 3, wherein the tertiary phosphine is a triarylphosphine.

5. A process as claimed in claim 1, wherein the base is selected from secondary and tertiary amines.

6. A process as claimed in claim 1, wherein the reaction is carried out at a temperature in the range from 50 to 250° C.

7. A process as claimed in claim 1, wherein the 1,3-diketone of the formula III or its tautomers III' and III'' are of the formula IIIa or IIIb:

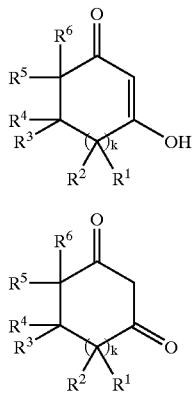

in which k is 0, 1 or 2 and the variables $R^1$ to $R^6$ are as defined below:

$R^1$, $R^5$ independently of one another are hydrogen, $C_1$–$C_4$-alkyl or $C_1$–$C_4$-alkoxycarbonyl;

$R^2$, $R^4$, $R^6$ independently of one another are hydrogen, $C_1$–$C_4$-alkyl, $C_1$–$C_4$-alkylthio or $C_1$–$C_4$-alkoxy;

$R^3$ is hydrogen, halogen, hydroxyl, $C_1$–$C_6$-alkyl, $C_1$–$C_6$-haloalkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkoxycarbonyl, $C_1$–$C_6$-haloalkoxycarbonyl; 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last mentioned radicals may be substituted by one to three $C_1$–$C_4$-alkyl radicals; or $R^2$ and $R^4$ or $R^4$ and $R^6$ together form a π bond or a $C_1$–$C_5$-alkanediyl chain which may have a π bond and/or may carry one, two or three radicals from the following group: halogen, cyano, $C_1$–$C_4$-alkyl, $C_1$–$C_4$-haloalkyl or $C_1$–$C_4$-alkoxycarbonyl; or $R^5$ and $R^6$ together form a $C_1$–$C_5$-alkanediyl chain which may have a π bond and/or may carry one, two or three radicals from the following group: halogen, cyano, $C_1$–$C_4$-alkyl, $C_1$–$C_4$-haloalkyl or $C_1$–$C_4$-alkoxycarbonyl; or $R^2$ and $R^6$ together form a $C_1$–$C_4$-alkanediyl chain which may have a π bond and/or may carry one, two or three radicals from the following group: halogen, cyano, $C_1$–$C_4$-alkyl, $C_1$–$C_4$-haloalkyl or $C_1$–$C_4$-alkoxycarbonyl; or $R^3$ and $R^4$ together form a chain of the formula —O—$(CH_2)_p$—O—, —O—$(CH_2)_p$—S—, —S—$(CH_2)_p$—S—, —O—$(CH_2)_q$— or —S—$(CH_2)_q$—, in which p is 2, 3, 4 or 5 and q is 2, 3, 4, 5 or 6 and which may be substituted by one, two or three radicals from the following group: halogen, cyano, $C_1$–$C_4$-alkyl, $C_1$–$C_4$-haloalkyl or $C_1$–$C_4$-alkoxycarbonyl; or $R^3$ and $R^4$ together with the carbon to which they are attached form a carbonyl or thiocarbonyl group.

8. A process as claimed in claim 1, wherein the aryl halide of the formula II is represented by the formula IIa:

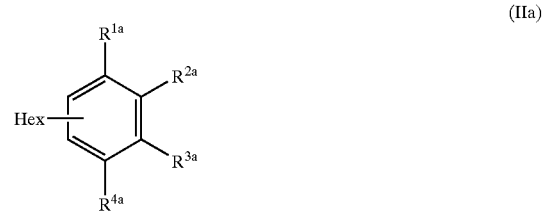

in which $R^{1a}$ and $R^{4a}$ independently of one another are hydrogen, halogen, in particular fluorine or chlorine, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, hydroxy-$C_1$–$C_6$-alkyl, $C_1$–$C_6$-alkylsulfonyl, $C_1$–$C_6$-haloalkylsulfonyl, $C_1$–$C_6$-alkoxy-$C_1$–$C_6$-alkyl, $C_1$–$C_6$-alkylthio-$C_1$–$C_6$-alkyl, $C_1$–$C_6$-haloalkylthio-$C_1$–$C_6$-alkyl, $C_1$–$C_6$-alkylsulfonyl-$C_1$–$C_6$-alkyl, $C_1$–$C_6$-haloalkylsulfonyl-$C_1$–$C_6$-alkyl, $C_1$–$C_6$-alkylamino-$C_1$–$C_6$-alkyl, or di($C_1$–$C_6$-alkyl)amino-$C_1$–$C_6$-alkyl and $R^{2a}$ and $R^{3a}$ form a 5- or 6-membered saturated or unsaturated heterocycle which may have 1, 2 or 3 heteroatoms selected from the group consisting of N, S and O, where sulfur atoms in the heterocycle may also be present as sulfoxide or sulfone, nitrogen atoms and carbon atoms in the heterocycle have a hydrogen atom or a substituent selected from the group consisting of halogen, nitro, cyano, hydroxyl, amino, $C_1$–$C_6$-alkyl, $C_1$–$C_6$-haloalkyl, $C_1$–$C_6$-aminoalkyl, $C_1$–$C_6$-alkylcarbonyl, $C_1$–$C_6$-alkylcarbonyloxy, $C_1$–$C_6$-alkyloxycarbonyl, $C_1$–$C_6$-alkoxy-$C_1$–$C_6$-alkyl, $C_1$–$C_6$-alkylcarbonyl-$C_1$–$C_6$-alkyl, $C_1$–$C_6$-alkoxy, $C_1$–$C_6$-haloalkoxy, $C_2$–$C_6$-alkenyl, $C_2$–$C_6$-alkynyl, $C_1$–$C_6$-hydroxyalkoxy, $C_1$–$C_6$-alkoxy-$C_1$–$C_6$-alkoxy, $C_3$–$C_6$-cycloalkyl, $C_3$–$C_8$-cycloalkoxy, $C_1$–$C_6$-alkylthio, $C_1$–$C_6$-haloalkylthio, $C_1$–$C_6$-hydrokyalkylthio, $C_1$–$C_6$-alkoxy-$C_1$–$C_6$-alkylthio, phenyl, phenyl-$C_1$–$C_6$-alkyl, phenylcarbonyl, phenylcarbonyloxy, phenoxycarbonyl, 5-, 6- or 7-membered heterocyclyl, phenoxy, phenylamino, diphenylamino, heterocyclyl-$C_1$–$C_6$-alkyl, heterocyclyloxy, heterocyclylcarbonyl, heterocyclyloxycarbonyl, heterocyclylcarbonyloxy, where the phenyl and heterocyclyl groups of the 14 last-mentioned radicals may for their part be partially of fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy, $C_1$–$C_6$-alkylamino, di-$C_1$–$C_6$-alkylamino, $C_3$–$C_6$-cycloalkylamino, where the alkyl and cycloalkyl groups of the three last-mentioned radicals may be partially or fully halogenated and/or may carry one to three substituents selected from the group consisting of $C_1$–$C_4$-alkoxy or hydroxyl, where carbon ring members may also be present as carbonyl function, thiocarbonyl function, oxime or oxime ether function; or $R^{1a}$ and $R^{2a}$ or $R^{3a}$ and $R^{4a}$ form a 5- or 6-membered saturated or unsaturated heterocycle which may have 1, 2 or 3 heteroatoms selected from the group consisting of N, S and O, where the ring atoms of the heterocycle may be substituted in the manner described above; and the remaining radicals $R^{1a}$, $R^{2a}$, $R^{3a}$ and $R^{4a}$ independently of one another have the meanings mentioned for $R^{1a}$, or $R^{2a}$ is hydrogen or 5-, 6- or 7-membered heterocyclyl which has 1, 2 or 3 hetero atoms selected from the group consisting of N, S and O, where the ring atoms of the heterocycle may be substituted in the manner described above; and $R^{1a}$, $R^{3a}$ and $R^{4a}$ independently of one another have the meanings mentioned above for $R^{1a}$.

9. A process as claimed in claim 8, wherein the aryl halide II is represented by the formula IIb:

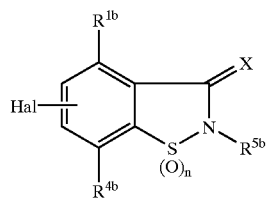

(IIb)

in which Hal is as defined above and $R^{1b}$ and $R^{4b}$ have the meanings mentioned above for $R^{1a}$ and $R^{4a}$, respectively, $R^{5b}$ is hydrogen, $C_1$–$C_6$-alkyl, $C_1$–$C_6$-haloalkyl, $C_1$–$C_6$-alkylcarbonyl, $C_1$–$C_6$-alkoxy-$C_1$–$C_6$-alkyl, $C_2$–$C_6$-alkenyl, $C_2$–$C_6$-alkynyl, $C_1$–$C_6$-hydroxyalkoxy, $C_1$–$C_6$-alkoxy-$C_1$–$C_6$-alkoxy, $C_3$–$C_8$-cycloalkyl, phenyl, phenyl-$C_1$–$C_6$-alkyl, where phenyl in the two last-mentioned groups may carry one, two or three substituents selected from the group consisting of halogen, nitro, cyano, hydroxyl, $C_1$–$C_4$-alkyl, $C_1$–$C_4$-haloalkyl, $C_1$–$C_4$-alkoxy and $C_1$–$C_4$-haloalkoxy, n is 0, 1 or 2 and X is oxygen or sulfur.

10. A process as claimed in claim 8, wherein the aryl halide II is represented by the formula IIc:

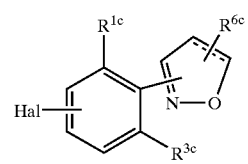

(IIc)

in which Hal is as defined above and $R^{1c}$ has the meanings given for $R^{1a}$, $R^{3c}$ is halogen, $C_1$–$C_6$-alkyl, $C_1$–$C_6$-haloalkyl, $C_1$–$C_6$-alkylthio, $C_1$–$C_6$-alkylsulfinyl, $C_1$–$C_6$-alkylsulfonyl, $C_1$–$C_6$-alkoxy or $C_1$–$C_6$-haloalkoxy, === is a double bond or a single bond and $R^{6c}$ is hydrogen or $C_1$–$C_4$-alkyl.

11. A process as claimed in claim 8, wherein the aryl halide II is represented by the formula IId:

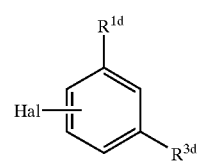

(IId)

in which Hal is as defined above and $R^{1d}$ has the meanings mentioned for $R^{1a}$ and $R^{3d}$ is halogen, $C_1$–$C_6$-alkyl, $C_1$–$C_6$-haloalkyl, $C_1$–$C_6$-alkylthio, $C_1$–$C_6$-alkylsulfinyl, $C_1$–$C_6$-alkylsulfonyl, $C_1$–$C_6$-alkoxy or $C_1$–$C_6$-haloalkoxy.

12. A process for preparing 2-aroyl-substituted 1,3-diketones of the formula X or their tautomer Xa, Xb or Xc

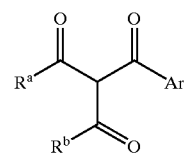

(X)

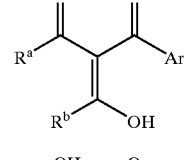

(Xa)

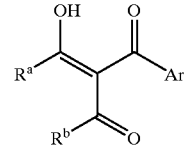

(Xb)

-continued

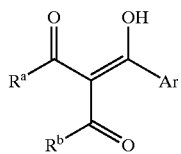

(Xc)

in which $R^a$, $R^b$, and Ar are as defined in claim 1, which comprises the following reaction steps:

1. Reaction of a 1,3-diketone of the formula III defined in claim 1 or its tautomers III' or III" with an aryl halide Ar-Hal in which Hal is chlorine, bromine or iodine in a carbon monoxide atmosphere in the presence of a base and a transition metal catalyst which comprises at least one transition metal of group VIII of the Periodic Table of the Elements to give a β-ketoenol ester of the formula Ia or Ib defined in claim 1 and, 2. rearrangement of the compound Ia or Ib to give a compound X or Xa, Xb and/or Xc by treatment of Ia and/or Ib with a base and a catalytically effective amount of at least one cyanide compound.

* * * * *